(12) United States Patent
Liu (10) Patent No.: US 9,131,733 B2
(45) Date of Patent: Sep. 15, 2015

(54) BATTERY ASSEMBLY AND ELECTRONIC CIGARETTE USING THE SAME

(71) Applicant: Qiuming Liu, Guangdong (CN)

(72) Inventor: Qiuming Liu, Guangdong (CN)

(73) Assignee: HUIZHOU KIMREE TECHNOLOGY CO., LTD. SHENZHEN BRANCH, Shenzhen (CN)

( * ) Notice: Subject to any disclaimer, the term of this patent is extended or adjusted under 35 U.S.C. 154(b) by 0 days.

(21) Appl. No.: 14/061,117

(22) Filed: Oct. 23, 2013

(65) Prior Publication Data
US 2015/0047660 A1    Feb. 19, 2015

(30) Foreign Application Priority Data
Aug. 16, 2013  (CN) .......................... 2013 2 0504288

(51) Int. Cl.
*A24F 47/00*    (2006.01)
*H02J 7/00*     (2006.01)
*A61M 15/06*    (2006.01)

(52) U.S. Cl.
CPC ............. *A24F 47/008* (2013.01); *A24F 47/002* (2013.01); *A61M 15/06* (2013.01); *H02J 7/0042* (2013.01)

(58) Field of Classification Search
CPC ....... A24F 7/002; A24F 47/008; A61M 15/06
USPC ............................. 131/273, 329; 128/202.21
See application file for complete search history.

(56) References Cited

U.S. PATENT DOCUMENTS

2014/0014124 A1*   1/2014   Glasberg et al. .............. 131/328

* cited by examiner

*Primary Examiner* — Anthony Calandra
(74) *Attorney, Agent, or Firm* — Locke Lord LLP; Tim Tingkang Xia, Esq.

(57) ABSTRACT

This present invention relates to the field of A battery assembly configured to be combined with an atomization assembly to form an electronic cigarette, comprising a battery, and the battery including a first battery electrode and a second battery electrode; wherein, the battery assembly further includes a first charging electrode electrically connected to the first battery electrode and a second charging electrode electrically connected to the second battery electrode, the first charging electrode extends to an end surface of the battery assembly, the second charging electrode partially or wholly surrounds a side wall of the battery assembly, and both the first charging electrode and the second charging electrode are configured for connecting with an external charger. By implementing the battery assembly of the present invention, the battery assembly and the electronic cigarette with the battery assembly can be directly charged, which makes charging be convenient.

12 Claims, 7 Drawing Sheets

BATTERY ASSEMBLY AND ELECTRONIC CIGARETTE USING THE SAME

CROSS-REFERENCE TO RELATED APPLICATIONS

This non-provisional application claims priorities under 35 U.S.C. §119(a) on Patent Application No. 201320504288.7 filed in P.R. China on Aug. 16, 2013, the entire contents of which are hereby incorporated by reference.

FIELD OF THE INVENTION

This present invention relates to the field of electrical heating products, and more particularly to a battery assembly and an electronic cigarette.

BACKGROUND OF THE INVENTION

An electronic cigarette generally comprises an atomization assembly and a battery assembly. In an electronic cigarette of the prior art, the methods for connecting the atomization assembly with the battery assembly usually include a threaded connection method and a direct insertion connection method. A charging port of the electronic cigarette is an electrode connecting member of the battery assembly connected with the atomization assembly. When charging the electronic cigarette, the atomization assembly needs to be detached from the battery assembly, and the battery assembly needs to be inserted in a charger, so that a battery in the battery assembly can be charged. When adopting the aforementioned charging method, the operations may consume much time and labor. Furthermore, the atomization assembly is prone to be lost when it is detached from the battery assembly, which brings much inconvenience to users. Meanwhile, since a disposable electronic cigarette of the prior art is unable to be charged, if power of the battery is exhausted while tobacco tar is not finished, the tobacco tar may be unable to be continuously used, which makes the use of the disposable electronic cigarette be inconvenient.

SUMMARY OF THE INVENTION

The object of the present invention is to provide a battery assembly that is capable of charging directly and an electronic cigarette using the same to solve the problem that the electronic cigarette and the battery assembly of the prior art are inconvenient to be charged.

In order to realize the object mentioned above, this present invention relates to a battery assembly configured to be combined with an atomization assembly to form an electronic cigarette, comprising a battery, and the battery including a first battery electrode and a second battery electrode; the battery assembly further includes a first charging electrode electrically connected to the first battery electrode and a second charging electrode electrically connected to the second battery electrode, the first charging electrode extends to an end surface of the battery assembly, the second charging electrode partially or wholly surrounds a side wall of the battery assembly, and both the first charging electrode and the second charging electrode are configured for connecting with an external charger.

The battery assembly further includes an end cover mounted on an end of the battery assembly, and the first charging electrode axially runs through the end cover.

The battery assembly further includes a cigarette butt lamp configured for simulating burning tobacco, and the end cover is a lamp cap covered on the cigarette butt lamp.

The end cover includes an end cover body, and a diameter of an end of the end cover body gradually reduces relative to the end cover body to form an inserting portion; the battery assembly includes a battery sleeve configured for accommodating the battery, and the inserting portion is inserted in the battery sleeve.

The second charging electrode is sheathed on the inserting portion, and two ends of the second charging electrode are abutted against an end of the end cover body and an end of the battery sleeve respectively.

A control unit configured for controlling the atomization assembly to work is accommodated in the battery sleeve, and the control unit is disposed between the battery and the end cover; the control unit is configured for controlling both electricity supply from the battery to the atomization assembly and atomizing work of the atomization assembly when the electronic cigarette is working normally, and the control unit is further configured for cutting the electricity supply from the battery to the atomization assembly when the electronic cigarette is charged.

The first charging electrode is electrically connected to the first battery electrode via the control unit by a first connecting line, and the second charging electrode is electrically connected to the second battery electrode by a second connecting line; the control unit is provided with a second connecting terminal, an end of the battery assembly far away from the end cover is provided with an outer electrode, and the outer electrode is successively connected to the second battery electrode and the second connecting terminal by a fourth connecting line.

An end surface of the first charging electrode and an end surface of the battery assembly cooperatively form a plat surface.

The battery assembly includes a battery sleeve configured for accommodating the battery, and the second charging electrode is a metal ring or a plating layer surrounding a side wall of the battery sleeve.

This present invention further relates to an electronic cigarette comprising an atomization assembly and a battery assembly, the battery assembly including a battery, and the battery including a first battery electrode and a second battery electrode; the battery assembly further includes a first charging electrode electrically connected to the first battery electrode and a second charging electrode electrically connected to the second battery electrode, the first charging electrode extends to an end surface of the battery assembly, the second charging electrode partially or wholly surrounds a side wall of the battery assembly, and both the first charging electrode and the second charging electrode are configured for connecting with an external charger.

The battery assembly further includes an end cover mounted on an end of the battery assembly, and the first charging electrode axially runs through the end cover.

The battery assembly further includes a cigarette butt lamp configured for simulating burning tobacco, and the end cover is a lamp cap covered on the cigarette butt lamp.

The end cover includes an end cover body, and a diameter of an end of the end cover body gradually reduces relative to the end cover body to form an inserting portion; the battery assembly includes a battery sleeve configured for accommodating the battery, and the inserting portion is inserted in the battery sleeve.

The second charging electrode is sheathed on the inserting portion, and two ends of the second charging electrode are abutted against an end of the end cover body and an end of the battery sleeve respectively.

A control unit configured for controlling the atomization assembly to work is accommodated in the battery sleeve, and the control unit is disposed between the battery and the end cover; the control unit is configured for controlling both electricity supply from the battery to the atomization assembly and atomizing work of the atomization assembly when the electronic cigarette is working normally, and the control unit is further configured for cutting the electricity supply from the battery to the atomization assembly when the electronic cigarette is charged.

The first charging electrode is electrically connected to the first battery electrode via the control unit by a first connecting line, and the second charging electrode is electrically connected to the second battery electrode by a second connecting line; the control unit is provided with a second connecting terminal, an end of the battery assembly far away from the end cover is provided with an outer electrode, and the outer electrode is successively connected to the second battery electrode and the second connecting terminal by a fourth connecting line.

An end surface of the first charging electrode and an end surface of the battery assembly cooperatively form a plat surface.

The battery assembly includes a battery sleeve configured for accommodating the battery, and the second charging electrode is a metal ring or a plating layer surrounding a side wall of the battery sleeve.

By implementing the battery component and the electronic cigarette of the present invention, the following advantages can be achieved: because the charging electrode of the electronic cigarette of the present invention includes a first charging electrode mounted on the end cover and a second charging electrode mounted on the end of the battery assembly near the end cover, in the charging process, both the first charging electrode and the second charging electrode can be merely inserted in an external charger, which makes the charging process be convenient. Meanwhile, when the present invention is implemented in an electronic cigarette capable of being used for many times, the atomization assembly does not need to be detached from the battery assembly in the charging process. In this way, a defect that the atomization assembly is prone to be lost when the atomization assembly is detached from the battery assembly is avoided.

DETAILED DESCRIPTION OF THE PREFERRED EMBODIMENT

In order to understand the technical features, the purpose and the effect of the present invention more clearly, the specific embodiments of the present invention will be described in detail referring to the drawings.

Referring to FIGS. 1-5, the present invention relates to a battery assembly 2 configured to be combined with an atomization assembly 1 to form an electronic cigarette. The battery assembly 2 includes a battery 22, and the battery 2 includes a first battery electrode 221 and a second battery electrode 222. The battery assembly 2 further includes a first charging electrode 31 connected to the first battery electrode 221 and a second charging electrode 32 connected to the second battery electrode 222. The first charging electrode 31 is mounted at an end of the battery assembly 2 and extends to an end surface of the battery assembly 2, and the second charging electrode 32 partially or wholly surrounds a side wall of the battery assembly 2. Both the first charging electrode 31 and the second charging electrode 32 are configured for connecting with an external charger.

Figure 4:
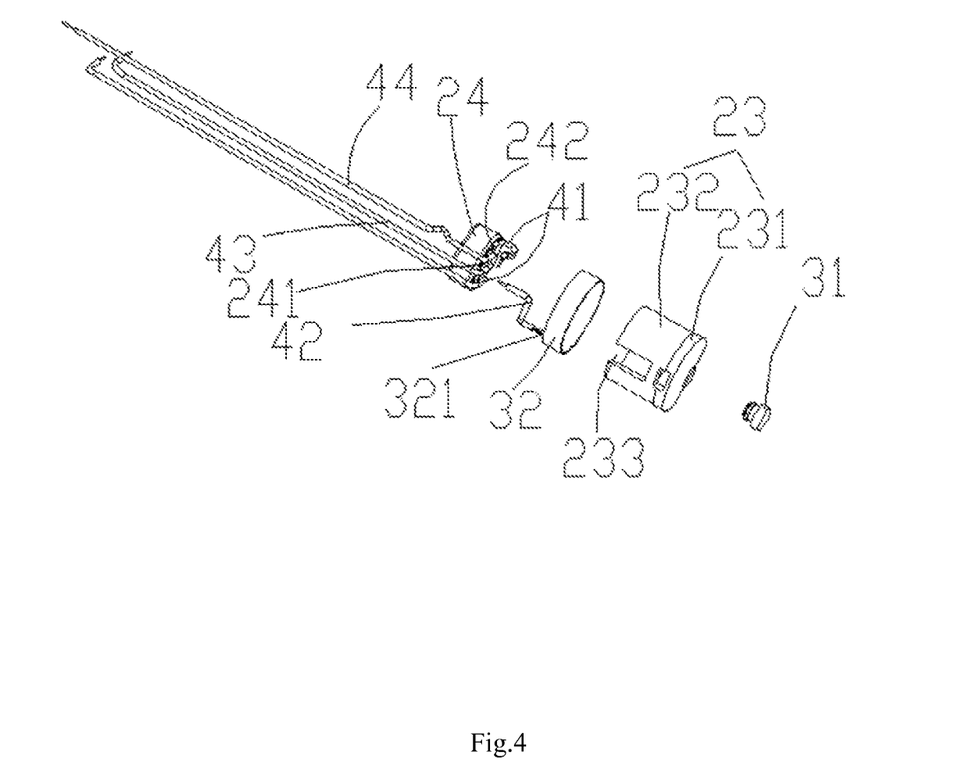
FIG. 4 is a disassembled structural view of one part of a battery assembly of the present invention.
Figure 5:
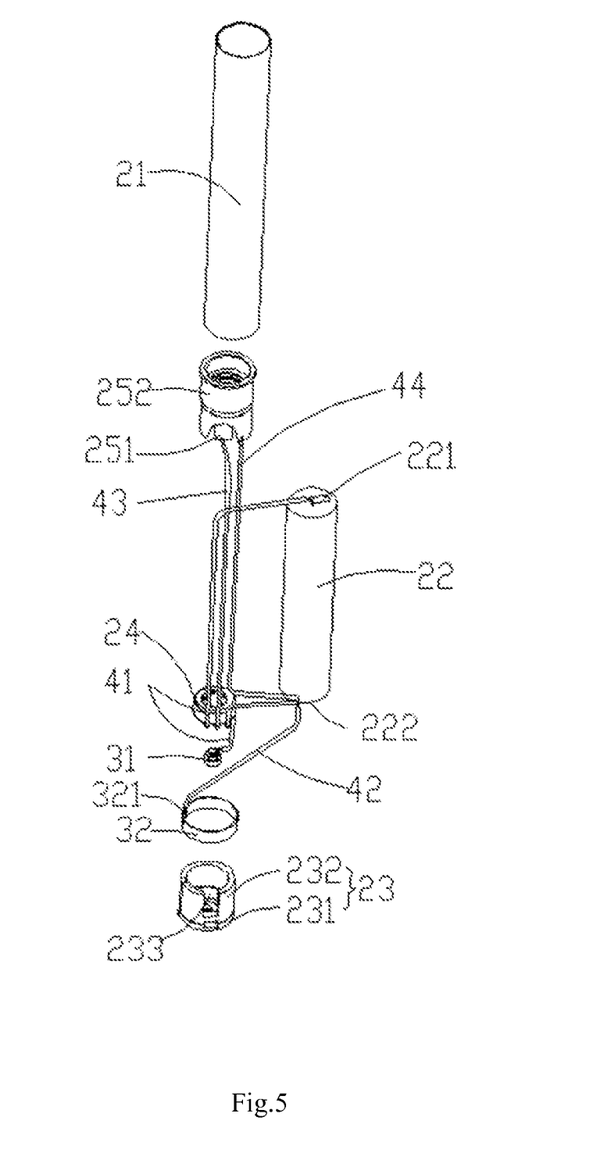
FIG. 5 is a disassembled structural view of another part of the battery component of the present invention.

Referring to FIG. 4 and FIG. 5, preferably, the second charging electrode 32 is a ring-shaped conductive piece.

An end cover 23 is mounted on an end of the battery assembly 2, and the first charging electrode 31 axially runs through the end cover 23. The battery assembly 2 further includes a cigarette butt lamp configured for simulating burning tobacco, and the end cover 23 can also be a lamp cap covered on the cigarette butt lamp.

The end cover 23 includes an end cover body 231, and a diameter of an end of the end cover body 231 gradually reduces relative to the end cover body 231 to form an inserting portion 232. The battery assembly 2 further includes a battery sleeve 21 configured for accommodating the battery 22, and the inserting portion 232 is inserted inside the battery sleeve 21. In this embodiment, the inserting portion 232 is inserted in the battery sleeve 21 and forms interference fit with the battery sleeve 21.

Figure 1:
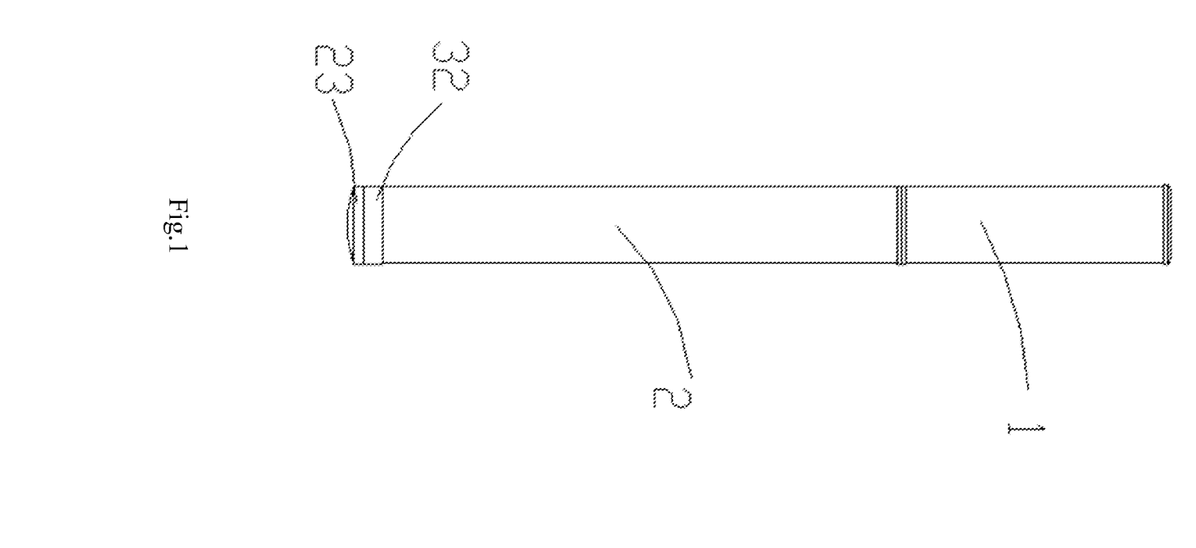
FIG. 1 is a whole schematic view of an electronic cigarette of the present invention.
Figure 2:
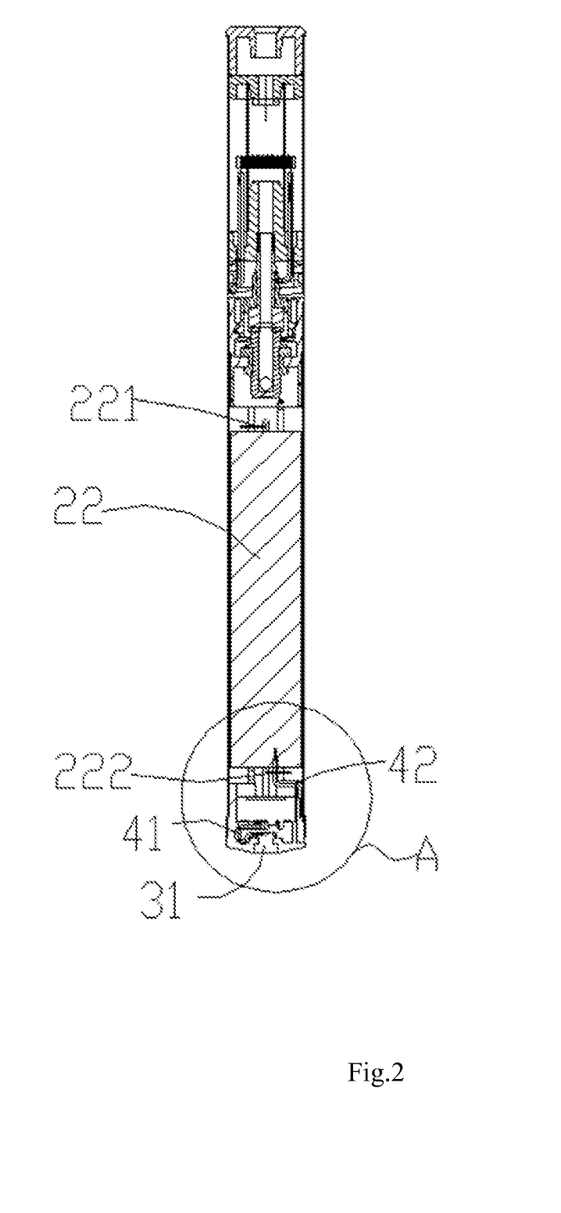
FIG. 2 is a whole cut-away view of the electronic cigarette of the present invention.
Figure 3:
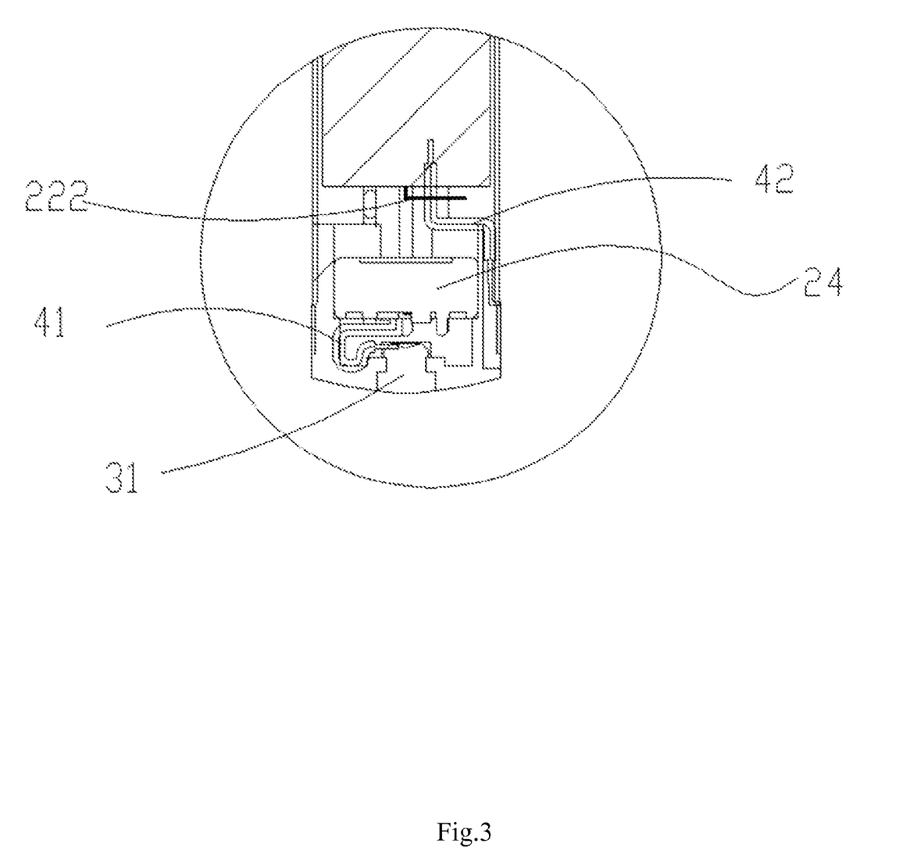
FIG. 3 is an enlarged view of the Part A shown in FIG. 2.

When the battery assembly 2 and atomization assembly 1 of the present invention are combined with each other to form the electronic cigarette, the atomization assembly 1 is connected to an end of the battery assembly 2 that is far away from the end cover 23. When the electronic cigarette is charged, only one end of the electronic cigarette where the battery assembly 2 is positioned needs to be inserted in a corresponding part of a charger to charge the battery 22, so that the charging operations are easy. When the present invention is implemented in an electronic cigarette capable of being used for many times, as the atomization assembly 1 does not need to be detached from the battery assembly 2, the atomization assembly 1 is not easy to be lost. When the present invention is implemented in a disposable electronic cigarette, the atomization assembly 1 cannot be detached from the battery assembly 2. Thus, by mounting the first charging electrode 31 and the second charging electrode 32 on the battery assembly 2, the battery 22 can be conveniently charged.

The first charging electrode 31 axially runs through an end of the end cover body 231 and is electrically connected with the first battery electrode 221 of the battery 22. The first charging electrode 31 can run through the end cover body 231 by two methods. In one of the two methods, the end cover body 231 defines a first through-hole axially running through an end of the end cover body 231, and the first charging electrode 31 is inserted in the first through-hole with interference fit. In the other one of the two methods, the end cover 23 is made of soft material, and the end cover body 231 defines a second through-hole axially running through the end cover body 231; a flange protrudes from an inner wall of the end cover body 231 corresponding to the second through-hole, and the flange is disposed along a radial direction of the second through-hole; the first battery electrode 221 defines a recess corresponding the flange, and the flange is embedded into the recess.

An end surface of the first charging electrode 31 and an end surface of the battery assembly 2 cooperatively form a flat surface.

The second charging electrode 32 is sheathed on the inserting portion 232, and is electrically connected with the second battery electrode 222 of the battery 22. Two ends of the second charging electrode 32 are abutted against an end of the end cover body 231 and an end of the battery sleeve 21 respectively, so that the second charging electrode 32 is fixed between the end cover body 231 and the battery sleeve 21. For beautifying an appearance of the battery assembly 2, an outer surface of the second charging electrode 32 is positioned to be coplanar with an outer surface of the battery assembly 2.

Referring to FIG. 5, an end of the second charging electrode 32 facing the atomization assembly 1 extends inward along a radial direction of the battery assembly 2 and is bent away from the end cover body 231 along an axial direction of the battery assembly 2 to form a mounting part 321. That is, the mounting part 321 is a fold-fin. A second connecting line 42 is mounted on the mounting part 321, an accommodating portion 233 fitting a shape of the mounting part 321 is formed on the inserting portion 232, and the mounting part 321 is held in the accommodating portion 233. The accommodating portion 233 is a notch or a groove formed along an axial direction of the inserting portion 232 and opening toward an end of the inserting portion 232. In assembly of the second charging electrode 32, the second charging electrode 32 is sheathed on the inserting portion 232, and then a sub-assembly formed by the inserting portion 232 and the second battery electrode 32 is inserted in the battery sleeve 21. The mounting part 321 is completely received in the accommodating portion 233, so that the sub-assembly formed by the inserting portion 232 and the second battery electrode 32 can be conveniently inserted in the battery sleeve 21.

A control unit 24 configured for controlling the atomization assembly 1 to work is accommodated in the battery sleeve 21, and the control unit 24 is disposed between the battery 22 and the end cover 23. When the electronic cigarette is working normally, the control unit 24 is configured for controlling electricity supply from the battery 22 to the atomization assembly 1, and thereby further controlling atomizing work of the atomization assembly 1. When the electronic cigarette is charged, the control unit 24 is further configured for cutting the electricity supply from the battery 22 to the atomization assembly 1.

Specifically, the battery assembly 2 further includes an airflow sensor connected to the control unit 24. When the airflow sensor detects a change of smoking flow, the control unit 24 can control the atomization assembly 1 to start working or stop working.

Referring to FIG. 5, the first charging electrode 31 is electrically connected to the first battery electrode 221 via the control unit 24 by a first connecting line 41, and the second charging electrode 32 is electrically connected to the second battery electrode 222 by the second connecting line 42, so that the battery 22 is charged when charging the electronic cigarette.

The control unit 24 is provided with a first connecting terminal 241 and a second connecting terminal 242. An end of the battery assembly 2 far away from the end cover 23 is provided with an outer electrode 252, and the outer electrode 252 sleeves an inner electrode 251 therein. The inner electrode 251 is connected to the first connecting terminal 241 by a third connecting line 43, and the outer electrode 252 is successively connected to the second battery electrode 222 and the second connecting terminal 242 by a fourth connecting line 44. The control unit 24 is connected with the outer electrode 252, and is further connected with the atomization assembly 1, so that the control unit 24 controls the electricity supply from the battery 22 to the atomization assembly 1. In this present invention, the control unit 24 controls a voltage input by the charger, so that the battery 22 can be protected from being damaged by too high charging voltages.

In this embodiment, both a connection between the first connecting line 41 and the first charging electrode 31 and a connection between the first connecting line 41 and the first battery electrode 221 are formed by welding. Similarly, a connection between the second connecting line 42 and the second charging electrode 32, a connection between the second connecting line 42 and the second battery electrode 222, a connection between the third connecting line 43 and the inner electrode 251, a connection between the third connecting line 43 and the first connecting terminal 241, a connection between the fourth connecting line 44 and the outer electrode 252, and a connection between the fourth connecting line 44 and the second connecting terminal 242 are all formed by welding.

Moreover, in this present invention, the first battery electrode 221 means a positive electrode of the battery 22, and the second battery electrode 222 means a negative electrode of the battery 22.

This invention further relates to an electronic cigarette, and the electronic cigarette comprises the aforementioned battery assembly 2 and atomization assembly 1.

Figure 6:
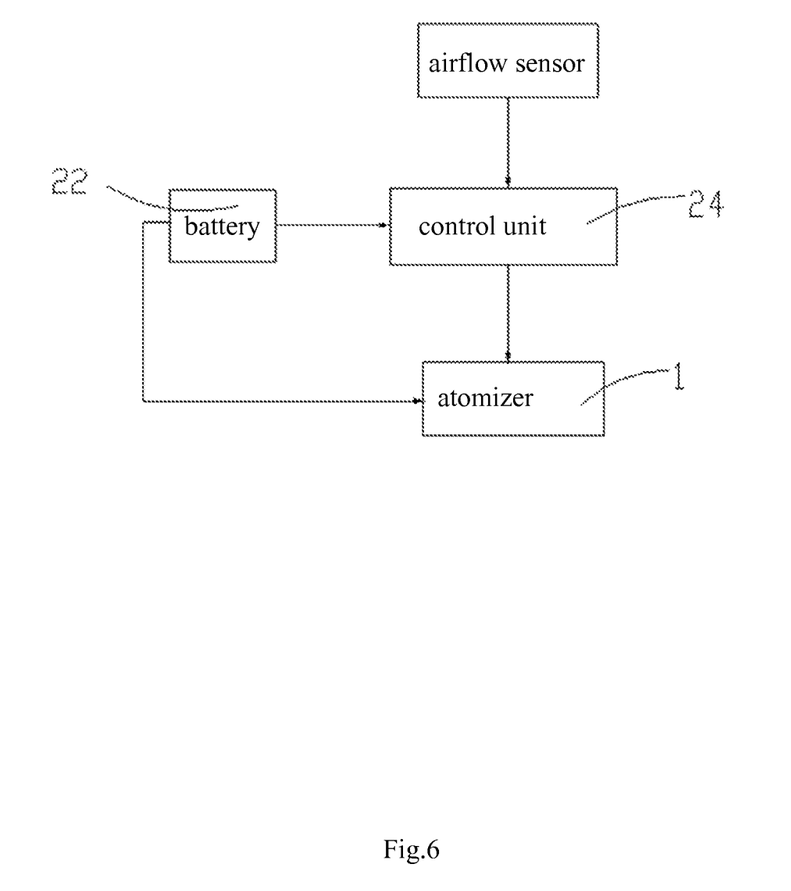
FIG. 6 is a schematic view of working principle of an electronic cigarette of the present invention in a no-charging status.

FIG. 6 shows a principle diagram of the electronic cigarette of the present invention in a no-charging status: the battery 22 is connected to the atomization assembly 1 and the control unit 24 respectively for supplying electricity to the control unit 24 and the atomization assembly 1 respectively. The airflow sensor is connected to the control unit 24, and is configured for generating a smoking start signal or a smoking end signal when the airflow sensor detects a change of air flow in smoking. Furthermore, the airflow sensor transmits the smoking start signal and the smoking end signal to the control unit 24, so that the control unit 24 controls the atomization assembly 1 to start smoking and to stop smoking according to the smoking start signal and the smoking end signal.

Figure 7:
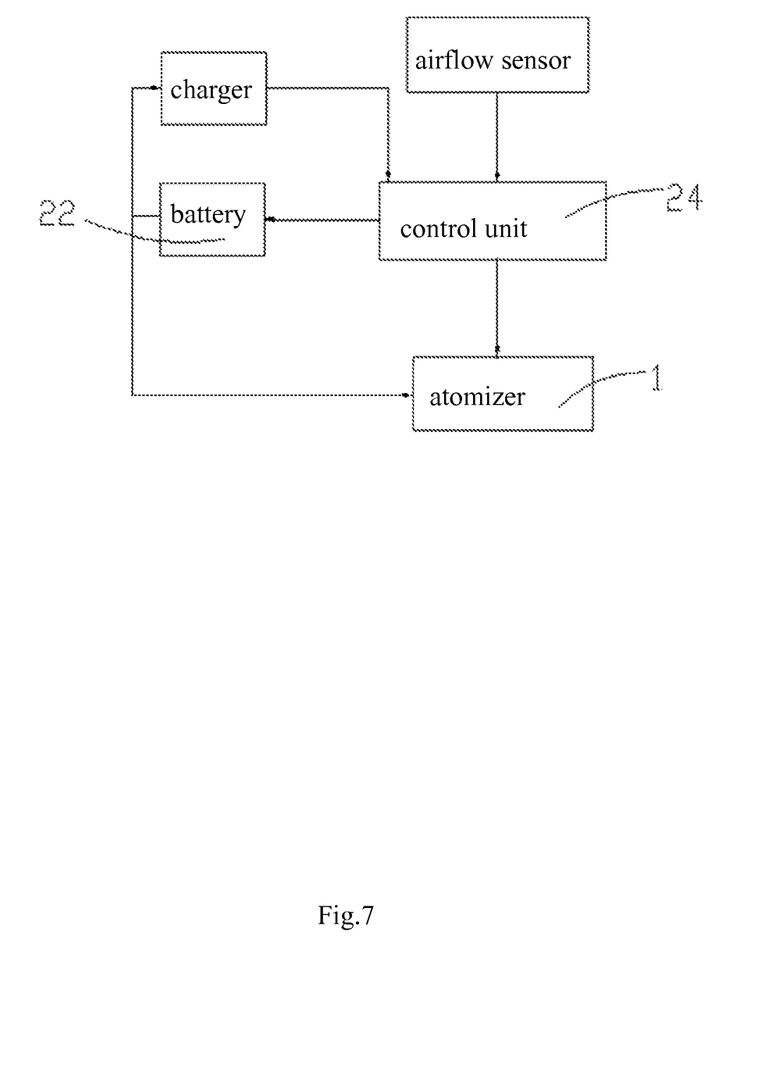
FIG. 7 is a schematic view of working principle of an electronic cigarette of the present invention in a charging status.

FIG. 7 shows a principle diagram of the electronic cigarette of the present invention in a charging status. Wherein, a charging voltage of the charger is controlled by the control unit 24, and the battery 22 is charged by the charging voltage.

In conclusion, the battery assembly 2 and the electronic cigarette of the present invention employ the first charging electrode 31 mounted on the end cover 23, and the second charging electrode 32 mounted on a portion of the battery assembly 2 near an end of the end cover 23 and partially or wholly surrounding around the battery assembly 2. In the charging process, both the first charging electrode 31 and the second charging electrode 32 can be merely inserted in an external charger, so that charging operating time can be saved. Meanwhile, when the present invention is implemented in an electronic cigarette capable of being used for many times, the atomization assembly 1 does not need to be detached from the battery assembly 2 in the charging process. In this way, a defect that the atomization assembly 1 is prone to be lost when the atomization assembly 1 is detached from the battery assembly 2 is avoided.

The present invention has been described with the drawings to the embodiments, while the present invention is not limit to the aforementioned specific embodiments and the specific embodiments are merely a hint rather than a limit. It will be understood by those skilled in the art that various changes may be made and equivalents may be substituted without departing from the purpose of the invention and the scope of the claims, but all the changes will be included within the scope of the appended claims.

What is claimed is:

1. A battery assembly configured to be combined with an atomization assembly to form an electronic cigarette, comprising
    a battery with a first battery electrode and a second battery electrode;
    a battery sleeve configured for accommodating the battery;
    a first charging electrode electrically connected to the first battery electrode;
    a second charging electrode electrically connected to the second battery electrode;
    the first charging electrode extends to an end surface of the battery assembly, the second charging electrode partially or wholly surrounds a side wall of the battery assembly; and
    both the first charging electrode and the second charging electrode are configured for connecting with an external charger;
    wherein the battery assembly further comprising an end cover mounted on an end of the battery assembly, the end cover includes an end cover body, and an inserting portion formed from an end of the end cover body with a step change of a diameter relative to the end cover body, the inserting portion is inserted in the battery sleeve; and
    the second charging electrode is sheathed on the inserting portion;
    two ends of the second charging electrode are abutted against an end of the end cover body and an end of the battery sleeve respectively;
    wherein one end of the two ends faces the atomization assembly, the end of the two ends extends inward along a radial direction of the battery assembly and is bent away from the end cover body along an axial direction of the battery assembly to form a mounting part, and the mounting part is a fold-fin, a second connecting line is mounted on the mounting part;
    an accommodating portion fitting a shape of the mounting part is formed on the inserting portion, and the mounting part is held in the accommodating portion.

2. The battery assembly of claim 1, wherein the battery assembly further includes a cigarette butt lamp configured for simulating burning tobacco, and the end cover is a lamp cap covered on the cigarette butt lamp.

3. The battery assembly of claim 1, wherein a control unit configured for controlling the atomization assembly to work is accommodated in the battery sleeve, and the control unit is disposed between the battery and the end cover;
    wherein the control unit is configured for controlling both electricity supply from the battery to the atomization assembly and atomizing work of the atomization assembly when the electronic cigarette is working normally, and the control unit is further configured for cutting the electricity supply from the battery to the atomization assembly when the electronic cigarette is charged.

4. The battery assembly of claim 3, wherein the first charging electrode is electrically connected to the first battery electrode via the control unit by a first connecting line, and the second charging electrode is electrically connected to the second battery electrode by the second connecting line; the control unit is provided with a second connecting terminal, an end of the battery assembly is provided with an outer electrode, the end of the battery assembly is away from the end cover, and the outer electrode is successively connected to the second battery electrode and the second connecting terminal by a fourth connecting line.

5. The battery assembly of claim 1, wherein an end surface of the first charging electrode and an end surface of the battery assembly cooperatively form a flat surface.

6. The battery assembly of claim 1, wherein the second charging electrode is a metal ring or a plating layer surrounding a side wall of the battery sleeve.

7. An electronic cigarette comprising an atomization assembly and a batter assembly, the battery assembly comprising
    a battery with a first battery electrode and a second battery electrode;
    a battery sleeve configured for accommodating the battery;
    a first charging electrode electrically connected to the first battery electrode;
    a second charging electrode electrically connected to the second battery electrode;
    the first charging electrode extends to an end surface of the battery assembly, the second charging electrode partially or wholly surrounds a side wall of the battery assembly; and
    both the first charging electrode and the second charging electrode are configured for connecting with an external charger;
    wherein the battery assembly further comprising an end cover mounted on an end of the battery assembly, the end cover includes an end cover body, and an inserting portion formed from an end of the end cover body with a step change of a diameter relative to the end cover body, the inserting portion is inserted in the battery sleeve; and
    the second charging electrode is sheathed on the inserting portion;
    two ends of the second charging electrode are abutted against an end of the end cover body and an end of the battery sleeve respectively;
    wherein one end of the two ends faces the atomization assembly, the end of the two ends extends inward along a radial direction of the battery assembly and is bent away from the end cover body along an axial direction of the battery assembly to form a mounting part, and the mounting part is a fold-fin, a second connecting line is mounted on the mounting part;
    an accommodating portion fitting a shape of the mounting part is formed on the inserting portion, and the mounting part is held in the accommodating portion.

8. The electronic cigarette of claim 7, wherein the battery assembly further includes a cigarette butt lamp configured for simulating burning tobacco, and the end cover is a lamp cap covered on the cigarette butt lamp.

9. The electronic cigarette of claim 7, wherein a control unit configured for controlling the atomization assembly to work is accommodated in the battery sleeve, and the control unit is disposed between the battery and the end cover;
    wherein the control unit is configured for controlling both electricity supply from the battery to the atomization assembly and atomizing work of the atomization assembly when the electronic cigarette is working normally, and the control unit is further configured for cutting the electricity supply from the battery to the atomization assembly when the electronic cigarette is charged.

10. The electronic cigarette of claim 9, wherein the first charging electrode is electrically connected to the first battery electrode via the control unit by a first connecting line, and the second charging electrode is electrically connected to the second battery electrode by the second connecting line; the control unit is provided with a second connecting terminal, an end of the battery assembly is provided with an outer electrode, the end of the battery assembly is away from the end cover, and the outer electrode is successively connected to the second battery electrode and the second connecting terminal by a fourth connecting line.

11. The electronic cigarette of claim 7, wherein an end surface of the first charging electrode and an end surface of the battery assembly cooperatively form a flat surface.

12. The electronic cigarette of claim 7, wherein the second charging electrode is a metal ring or a plating layer surrounding a side wall of the battery sleeve.

* * * * *